United States Patent [19]

Sechler

[11] Patent Number: 5,523,232
[45] Date of Patent: Jun. 4, 1996

[54] USE OF RESTRICTION ENDONUCLEASES AGAINST VIRUSES, INCLUDING HIV

[75] Inventor: Joan M. Sechler, Silver Spring, Md.

[73] Assignee: The United States of America as represented by the Department of Health and Human Services, Washington, D.C.

[21] Appl. No.: 257,625

[22] Filed: Jun. 8, 1994

Related U.S. Application Data

[63] Continuation-in-part of Ser. No. 861,938, Apr. 2, 1992, abandoned.

[51] Int. Cl.$^6$ .............................. C12N 7/04; A61K 38/46
[52] U.S. Cl. ..................... 435/236; 435/199; 424/94.6; 424/94.3
[58] Field of Search .................................. 435/236, 199; 424/94.6, 94.3

[56] References Cited

U.S. PATENT DOCUMENTS

| | | | |
|---|---|---|---|
| 4,179,337 | 12/1979 | Davis et al. | 435/181 |
| 4,895,724 | 1/1990 | Cardinal et al. | 424/418 |
| 5,006,333 | 4/1991 | Saifer et al. | 424/78 |
| 5,190,762 | 3/1993 | Yarosk | 424/450 |

FOREIGN PATENT DOCUMENTS

| | | |
|---|---|---|
| 0234781 | 9/1987 | European Pat. Off. |
| WO9212237 | 7/1992 | WIPO |

OTHER PUBLICATIONS

Schiffmann et al. (Mar. 1975) *Proc. Nat. Acad. Sci. USA* 72: 1059–1062, "N–Formylmethionyl Peptides as Chemoattractants for Leucocytes."

Kwoh et al. (Oct. 1986) *Proc. Nat. Acad. Sci. USA* 83: 7713–7717, "Introduction and Expression of the Bacterial PaeR7 Methylase Gene in Mammalian Cells."

Kwoh et al. (1988) *Nucleic Acids Research* 16(24): 11489–11506, "Introduction and Expression of the Bacterial PaeR7 Restriction Endonuclease Gene in Mouse Cells Containing the PaeR7 Methylase."

Avis (1990) "Parental Preparations," Ch. 84, pp. 1545–1553 in *Remington's Pharmaceutical Sciences*, 18th Edition, edited by Gennaro et al.

Gingeras (1991) *Modern Microbial Genetics*, pp. 301–321, "Restriction–Modification Systems: Genetic Sentries and Useful Systems in the Study of Molecular Genetics."

Prior (1991), Ch. 17, p. 445, in *Animal Cell Bioreactors*, edited by Ho et al., "Large–Scale Process Purification of Clinical Product from Animal Cell Cultures."

Colain, et al (1970) Ann. Oculist 203(4), 371–378.

Gutorov A. N., et al. (1976) Vestnik Dermatology and Venerolody 11, 75–78.

Demir, A. A. Lancet, Jun. 26, 1976.

Trukhachev, A. A., et al (1967) Virology 3, 552.

Anderson, P. M. et al. (1990) Can. Res. 50, 1853–1856.

Anderson, P., et al. (1981) Int. Immun. 31, 1099–1103.

*Primary Examiner*—Charles L. Patterson, Jr.
*Attorney, Agent, or Firm*—Foley & Lardner

[57] ABSTRACT

Restriction endonucleases are administered to a patient topically or internally to prevent or ameliorate viral infection. The endonucleases are also useful to treat products, such as blood and blood derived products, to eliminate viral transmission when the products are administered to a patient. In addition, the endonucleases may be used in the manner of a disinfectant to inactivate viral contamination on objects. The endonucleases are used in their native form, modified to provide decreased immunoreactivity or increased ability to target a site of infection or both, and alone or in combination with a suitable excipient. In addition to methods of treatment and disinfection, the invention provides related products, such as pharmaceutical compositions.

37 Claims, 5 Drawing Sheets

USE OF RESTRICTION ENDONUCLEASES AGAINST VIRUSES, INCLUDING HIV

CROSS-REFERENCE TO RELATED APPLICATIONS

This application is a continuation-in-part of U.S. Ser. No. 07/861,938, filed on Apr. 2, 1992 now abandoned.

BACKGROUND OF THE INVENTION

The present invention relates to the use of restriction endonucleases as therapeutic and disinfectant anti-viral agents.

There are currently very few effective anti-viral agents, although the many virally transmitted diseases account for much human suffering and mortality. Thus, there is a great need for safe and effective anti-viral agents that can serve in therapies for these diseases, including life-threatening and fatal diseases such as hepatitis and AIDS.

Bacterial cells long have been known to contain restriction-modification systems that protect them from viral infection. See, for instance, Gingeras, T., "Restriction-Modification Systems" in MODERN MICROBIAL GENETICS 301–321 (Wiley-Liss, Inc. 1991). A restriction-modification system generally operates through two complementing enzymatic activities, an endonucleolytic activity and a modification activity. The endonucleolytic activity involves recognition of a specific sequence in viral DNA and subsequent endonucleolytic cleavage across both strands of the DNA. The modification activity involves the same sequence recognition step followed by modification of a base in the sequence, which interferes with the cleavage activity of the endonuclease. Thus, host cell DNA modified by the endogenous modification enzyme, is protected from degradation by the restriction enzyme which destroys the unprotected DNA of infecting virus.

Restriction-modification systems like those of prokaryotes have not been found as pervasively in eukaryotic cells, although restriction endonucleases have been isolated from several eukaryotic sources. See Sklar et al. (1986) *J. Biol. Chem.* 261: 6806–6810 (*Chlamydomonas reinhardtii*) and Lao et al. (1986) *Sci. Sin.* (Series B) 29: 947–953 (human). The genomic DNA of eukaryotic cells contains modified bases, however these modifications differ in many ways from those of prokaryotes and perform functions unrelated to viral infection. Viruses that infect eukaryotic cells do not encounter the same endonucleolytic defenses that beset viruses invading prokaryotic cells.

Nonetheless, many viruses which infect eukaryotic cells possess, during at least one part of their life cycle, genomes that consist of double stranded DNA which can be cleaved readily by restriction endonucleases derived from a prokaryotic source. Furthermore, it is well-known that restriction endonuclease cleavage can prevent viral DNA, such as bacteriophage lambda DNA, from packaging to form infectious virus particles, and can also destroy the ability of DNA to transform cells in vitro using, for instance, calcium phosphate precipitation. Accordingly, there has been some speculation that providing a restriction-modification system to eukaryotic cells might provide a means to prevent viral infection.

Strategies for achieving this end heretofore have focused on introducing into eukaryotic cells genes that provide the endonuclease and the modification activities. Providing the modification activity was thought necessary to protect cellular DNA from being degraded by the restriction enzyme, i.e., to distinguish cellular and viral DNA so that the endonucleolytic activity would not degrade the cellular DNA. Progress along this avenue has not been promising, however.

For instance, Kwoh expressed the bacterial PaeR7 methylase gene in mouse Ltk cells to study the effect of PaeR7 methylation on replication and transcription of eukaryotic DNA. Kwoh et al., *Proc. Natl. Acad. Sci. USA* 83: 7713 (1986). Kwoh noted that cell lines expressing the PaeR7 methylase would be suitable to the introduction of the PaeR7 endonuclease and that cells with both enzymes would contain a restriction-modification system that might render them resistant to viral infection.

Subsequently, Kwoh studied the expression of both methylase and endonuclease in eukaryotic cells and assessed the ability of the exogenously derived restriction-modification system to retard viral infection. Kwoh et al., *Nuc. Acids Res.* 16: 11489 (1988). Kwoh did not observe increased resistance to infection by murine adenovirus, herpes simplex virus, or vaccinia virus in any of the cell lines that expressed the bacterial endonuclease, even though the enzyme was expressed. Thus, this particular approach to using restriction enzymes as antiviral agents has not been successful.

In attempting to explain the negative results, Kwoh speculated that the methylase in these experiments might have modified not only the genomic but also the viral DNA, thus preventing the endonuclease from affecting the viral DNA. Alternatively, eukaryotic glycosylation of a bacterial restriction enzyme might have interfered with its ability to cleave viral DNA. In this regard, glycosylation could affect the endonucleolytic activity directly, the ability of the enzyme to bind the DNA substrate, or the ability of the enzyme to penetrate the viral nucleocapsid to cleave viral DNA in situ.

In any event, the failure of restriction endonuclease expressed by eukaryotic cells to inhibit viral infection has militated against the possibility that restriction enzymes might be employed somehow to prevent or ameliorate viral infection of eukaryotic cells.

SUMMARY OF THE INVENTION

It is therefore an object of the present invention to provide means for using restriction enzymes to prevent or ameliorate viral infection by exposing the virus and infected cells to restriction enzymes or derivatives thereof.

Another object of the present invention is to provide means for inactivating virus in biologically derived products and products intended for biological uses that comprises treating the product with a restriction endonuclease or a derivative thereof.

A particular object of the invention in this regard is to provide means for inactivating virus in blood and blood-derived products that comprises treating the blood or blood product with a restriction endonuclease or derivative thereof.

Another object of the invention is to provide compositions that comprise restriction enzymes or derivatives thereof for inhibiting propagation of a virus, inactivating virus in a biologically derived product or a product intended for biological use, or for disinfecting an object.

In accomplishing the foregoing objectives, there has been provided in accordance with the present invention a method for inhibiting propagation of a virus, comprising the step of administering to a patient in a therapeutically effective amount a composition comprising a compound comprised of a moiety of a restriction endonuclease such that the compound displays endonucleolytic activity toward the DNA of the virus.

In accordance with another aspect of the invention there has been provided an ex vivo method to inactivate virus in blood or a blood-derived composition, comprising the step of exposing the blood or blood-derived composition to a compound comprised of a moiety of a restriction endonuclease that provides endonucleolytic activity of a type and in an amount effective to inactivate the virus.

In accordance with still another object of the invention there has been provided a pharmaceutical composition for topical administration, comprising (A) a substantially pure and pyrogen-free compound comprised of a moiety of a restriction endonuclease such that the compound displays endonucleolytic activity toward DNA of the virus at a site of infection to which the composition is applied; and (B) a pharmaceutically acceptable excipient for topical administration.

In yet another aspect of the invention there as been provided a pharmaceutical composition for systemic administration, comprising (A) a substantially pure and pyrogen free compound comprised of a moiety of a restriction endonuclease such that the compound displays endonucleolytic activity toward DNA of the virus at a site of infection; and (B) a pharmaceutically acceptable excipient for systemic administration.

In yet still another aspect of the invention there has been provided a disinfectant composition, comprising (A) a compound comprised of a moiety of a restriction endonuclease such that the compound displays endonucleolytic activity toward DNA of a virus when applied to an object to be disinfected; and (B) an inert carrier for disinfectant application.

In additional aspects of the invention, the compounds of the invention may be modified to decrease deleterious immunological side effects, as compared with unmodified compound, when administered to a patient, for instance, which may be accomplished by providing compounds substantially free of N-formyl methionine, and/or by conjugating the compounds to polyethylene glycol or polypropylene glycol, inter alia. Moreover, the restriction endonuclease moieties may be encapsulated by liposomes for therapeutic administration and/or ex vivo use.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

It has been discovered that simple exposure of virus and infected cells to restriction enzymes can prevent, retard or ameliorate viral infection. This phenomenon is all the more surprising in light of the documented failure of bacterial restriction enzymes expressed in eukaryotic cells to inhibit or ameliorate eukaryotic viral infection.

Restriction endonucleases can inhibit viral infection by mechanisms that act intracellularly or extracellularly. Many viral genomes are in the form of double-stranded DNA genomes during at least part of the viral life-cycle. Restriction enzymes can prevent propagation of these viruses by cleaving the double-stranded DNA so as to prevent replication, transcription, packaging or other essential viral functions that require intact double-stranded DNA.

Without being limited to any one mechanism, it is possible that restriction enzymes inhibit viral infection by cutting double-stranded DNA. By this mechanism, for those viruses that have double-stranded DNA genomes throughout their life cycle, restriction enzymes have the potential to cleave the genomic material throughout the life-cycle. In this case, a restriction enzyme can inactivate intact virus, insofar as it can penetrate the viral capsid in an active form. For viruses whose genomes are double-stranded during only part of their life cycle, restriction enzymes can cleave the viral genome only when it is double-stranded. Thus, for instance, since the double-stranded DNA of a retrovirus, such as HIV, is a replicative intermediate that occurs only inside the host cell, it is likely that only restriction enzymes active inside the cell provide protection from these viruses.

Whichever modality is operative, it will be appreciated that the invention is useful against a wide variety of viral infections, including at least all those viruses with genomes of double-stranded DNA during at least part of their life-cycle.

Notable among the double stranded DNA viruses that infect man and cause health problems are the Hepadnaviridae, for instance hepatitis B virus; the Papovaviridae, including HPV 1–48, some of which are associated with the development of carcinomas; the Adenoviridae; and the Herpesviridae, including, for instance, herpes simplex viruses 1 and 2, cytomegalovirus and Epstein-Barr virus. Many of these viruses are characterized by prolonged persistence in the body in a latent form, and recurrent clinical disease may occur throughout life.

Among the viruses whose genomes are double-stranded DNA during only part of their life-cycles are the parvoviruses and the retroviruses. Notable among the viruses of the latter class is the HIV virus, the etiological agent of ARC and AIDS.

It will be appreciated by one of ordinary skill that any restriction enzyme may be useful in the invention. Without being limited to one mechanism of inactivation, as set forth above, restriction enzymes may inactivate virus by cleaving viral DNA. In this case, the ability of an enzyme to inactivate a virus will depend upon how often and where it cuts the double-stranded DNA sequence of the virus. Accordingly, enzymes useful in the invention are those that cut a viral sequence so as to preclude viral propagation. Among the preferred enzymes of the invention are those that cut a viral sequence frequently (which can preclude proper religation) and/or in regions of essential viral function, since these are the most likely to inactivate a virus. The most highly preferred enzymes in this aspect of the invention cleave frequently in essential regions.

Patterns of restriction enzyme cleavage in a viral genome can be determined readily by computerized analysis when the nucleic acid sequence has been determined. Thus, restriction enzymes that cut a genome frequently and/or in essential regions can be identified as good candidates for use in the invention, such as in therapeutic applications.

Furthermore, several DNA sequence data bases have been established that automatically identify in all listed sequences the cleavage sites for all known restriction enzymes. Many complete viral sequences are presently entered in the databases, and more are being added all the time. The data bases can be accessed from remote terminals or can be purchased in CD-ROM form. The software for identifying cleavage sites also is readily available. Hence, it is generally a matter of routine to determine restriction enzyme cleavage sites in a DNA of known sequence.

Even when the exact sequence of a virus isn't known, the recognition sequence of a restriction enzyme, which determines its frequency of cutting a random sequence, provides a rough indication of its cutting frequency in a viral DNA. Enzymes that recognize a four base pair sequence will cut a random sequence DNA every 256 base pairs, on average, while those that recognize a six base pair sequence will cut every 4096 base pairs. The cutting frequency of most enzymes in natural DNAs follows this statistical rule, with some exceptions. Generally, more frequently cutting enzymes are more likely to damage irreparably an essential region of the viral nucleic acid sequence. Nonetheless, in a particular situation a less frequently cutting enzyme may be more desirable because, for instance, it cuts the viral DNA in a vital location, completely inactivating the virus, and it offers other practical advantages. Thus, the efficacy of an enzyme for use against a particular virus can be predicted from its recognition sequence, either specifically by reference to a known viral DNA sequence, or generally based on its average frequency of cutting. These predictions are useful to a first approximation to choosing enzymes for further testing.

In addition, enzymes that provide blunt ends are preferred in the invention. Some restriction enzymes upon cleaving DNA produce overlapping ends that can base-pair (reanneal) to reform an intact DNA. The hydrogen bonding between base pairs in the overlapping ends is often strong enough to keep the annealed fragments together. The more overlapping bases there are, the stronger the hydrogen bonding; although, it will be recognized that the hydrogen bonding in G:C base pairs is stronger than in A:T base pairs. Accordingly, independently of other considerations, fewer overlapping base-pairs are preferred, and blunt ends, which have no overlap, are most preferred in this regard.

It is worth noting that some enzymes exhibit "star" activity under "suboptimal" conditions, which provides altered or reduced specificity of cleavage. Although in a research setting it is usually desirable to avoid "star" activity, the reduced specificity of cleavage may be advantageous in a therapeutic application. First, reduced specificity results in the enzyme cutting the DNA more frequently, increasing the likelihood that it will inactivate virus. In addition, physiological conditions may be more conducive to star activity than the activity normally used for research purposes. Hence, as a practical matter, the "star" activity of a given restriction enzyme or derivative thereof may be more important in a therapeutic application.

Several compilations of restriction enzymes are available both in printed and computer readable forms. For one, many commercial suppliers provide catalogs that enumerate the recognition and cleavage specificity of the enzymes they offer. For instance, "NEW ENGLAND BIOLABS," "GIBCO BRL," "BOEHRINGER-MANNHEIM," "STRATAGENE," "PROMEGA," "UNITED STATES BIOCHEMICAL CORP.," and "PHARMACIA LKB" all currently provide catalogs that list the restriction enzymes they offer, and their sources, specificity and optimum conditions, inter alia. These catalogs have extensive bibliographies and are useful guides to selecting enzymes for use in the invention. Additional listings of enzymes appear periodically in the reference literature. Perhaps the best known are those published by Dr. Richard Roberts. See, for example, Roberts, Nucleic Acids Research 17 (Suppl.): r347 (1989). These compilations also supplement the primary literature which provides basic information about all the known restriction enzymes, all of which may be used in the invention.

For instance, it is readily determined from its known sequence that, among a great many others, the enzymes EcoRI, BamHI and XbaI cut the hepatitis B viral genome, and therefore are preferred enzymes of the invention. Likewise, it is readily determined from its sequence that, among a great many others, the enzymes AluI, AvaII, BsaJI, BstNI, DsaV, Fnu4HI, HaeIII, MaeIII, N1aIV, and NSiI cut DNA of the HIV virus and, therefore, are preferred enzymes of the invention.

The effectiveness of a restriction enzyme to inhibit viral propagation and infection, though it may be predicted as described above, is preferably assessed by in vitro and in vivo assays of infection. Using assays, as described herein, for instance, it is possible to identify restriction enzymes and combinations of restriction enzymes capable of inhibiting, precluding or ameliorating infection by any virus.

Such assays can be carried out first in cell culture to establish the potential of different enzymes to cleave a viral DNA in a way that deleteriously affects viral propagation. Preliminary studies of this type then are followed by studies in appropriate animal models. Finally, clinical studies will be carried out.

For instance, in accordance with the invention, in vitro assays of restriction enzyme inhibition of HIV infection can be followed by studies of the enzyme's ability to inhibit the progress of infection and disease when administered to monkeys exposed to or infected with simian immunodeficiency virus (SIV), an animal model of human ARC and AIDS.

SCID mice provide another animal model to assess the ability of enzymes in accordance with the invention to inhibit the progress of HIV infection. Human bone marrow can be transplanted into the SCID mice and then infected with HIV. Enzymes in accordance with the invention can be administered to the HIV infected mice and the effect of the enzymes on the progress of infection and the development of ARC and AIDS-like symptoms can be assessed.

Murine acquired immunodeficiency syndrome (MAIDS) is yet another animal model that can be used to assess the ability of particular enzymes to inhibit the progress of an AIDS-like disease. MAIDS is characterized by lymphadenopathy, splenomegaly, polyclonal gammopathy, and immunodeficiency. See, for example, Jolicoeur, *The FASEB Journal* 5:2398 (1991), and Klinken et al., *J. Immunol.* 140:1123 (1988). The syndrome is induced by injection of LP-BM5 virus, a derivative of Duplan-Laterjet virus, which contains a mixture of replication-competent B-tropic ecotropic and mink cell focus-induced viruses and a defective genome (BM5d) that is the proximal cause of MAIDS. Chattopadhyay et al., *J. Virol.* 65:4232 (1991). The use of the MAIDS model to examine the efficacy of enzyme-encapsulated liposomes is illustrated in Example 5.

Different viruses require different assay systems, since hosts and culture conditions suitable to different viruses vary greatly. Appropriate conditions have been described for culturing a great many viruses, however, and these conditions can be used to test the effect of exposing virus and/or host to restriction enzymes to determine the ability of the enzyme to inhibit viral infection. For one discussion of culture conditions for specific viruses see Chapter 17 in Fields and Knipe, Eds., FIELDS VIROLOGY, 2nd Ed., Raven Press, N.Y. (1990).

A host and/or virus can be exposed at various times during a course of infection, under varying conditions, in several amounts, and in a variety of excipients, to mention just a few relevant parameters that can be varied, to assess the potential of an enzyme to achieve a potentially therapeutic effect.

In accordance with the invention it will also generally be useful to assess the activity of the restriction enzyme or derivative in the conditions it will encounter in an application. Thus, candidate enzymes capable of inhibiting or preventing viral propagation can be tested for their ability to cleave known DNAs under the conditions in which they will be applied. For instance, the ability of an enzyme to inactivate hepatitis B virus in blood would be tested in part by cleaving a DNA, such as a plasmid DNA, or a viral DNA, in blood. Using a known DNA the activity of the enzyme can be assessed, and alterations to its usual activity profile can also be determined.

In addition to tests ex vivo in cultured cells, potential restriction enzyme therapeutic agents can be tested in animal models to assess prophylactic, ameliorative, therapeutic and/or curative potential, either alone or in conjunction with other therapeutic agents. In fact, in some cases it will not be possible to culture a virus and it will be necessary to perform all biological assays in animal models. It will be readily appreciated that different animal models will be appropriate to different viruses. Any animal model, however, can be used to assess the therapeutic potential of a restriction enzyme.

Thus, a potentially effective dose of a test enzyme may be administered to a suitable population of animals, and the effect of the enzyme on the course of a viral infection may be assessed by comparison with an appropriate control. Such methods for assessing pharmacological effect are well known in the art and can readily be adapted to determining the therapeutic profile of restriction enzymes. This approach is illustrated in Example 5, below.

Some restriction enzymes may be used in the invention unmodified as isolated, from bacterial cells for instance. However, the enzymes of the invention may also be modified forms of the naturally occurring enzymes. Such modified enzymes can be produced by a variety of well-known techniques such as recombinant DNA techniques, conjugation to other moieties and carriers, and chemical modification, inter alia. Thus, it will be appreciated that restriction enzymes of the invention include molecules that both preserve the cleavage activity of the natural enzyme and add additional structural features that provide properties desirable in an anti-viral application.

In general, the restriction enzymes of the invention provide at least one sequence recognition and endonucleolytic activity of a restriction enzyme, which may be called the active portion. The sequence recognition and endonucleolytic activities may be provided by an enzyme in its unmodified form isolated from its natural source or produced by recombinant DNA techniques, or they may be derived from the natural enzyme by recombinant DNA or protein chemistry techniques.

For instance, it will often be desirable to use a fragment of an enzyme that provides the sequence recognition and endonucleolytic activities, alone or combined with additional structural elements. Similarly, the natural enzyme or portion thereof may be modified to provide additional desirable characteristics.

Thus, the active portion of a restriction enzyme may be combined with other substituents and/or moieties by means well known in the art to provide such additional functions as decreased immunological reactivity, receptor or antigen binding or other targeting moieties, and delayed release, among others. In general, enzymes of the invention are comprised of a moiety of a restriction endonuclease such that the enzyme displays endonucleolytic activity toward DNA of a virus. The endonucleolytic activity in general will be effective in preventing, retarding, ameliorating or curing a viral infection.

A restriction endonuclease or derivative thereof may be modified to decrease undesirable immunological responses when it is administered to a patient, in comparison with the unmodified endonuclease or endonuclease derivative. In this regard, preferred enzymes and enzyme derivatives of the invention are those that are substantially non-immunogenic. That is to say, preferred embodiments of the invention are those in which administration of the enzyme to a patient does not engender an adverse immunological reaction that precludes its use as therapeutic agent. Among the most preferred embodiments of the invention are those enzymes and derivatives that are substantially non-immunogenic, i.e., engender little or no adverse immunological response. A variety of methods for ameliorating or eliminating deleterious immunological reactions of this sort can be used in accordance with the invention.

When the endonuclease is produced in prokaryotic cells, for instance, the initial methionine generally will be N-formylated. The N-formyl methionine in some instances has caused deleterious immunological responses upon injection of prokaryotic proteins into mammalian hosts, probably because it is a chemoattractant for leukocytes. See Schiffmann et al. (1975) *Proc. Nat'l Acad. Sci.* 72: 1059–1062. To avoid such complications, a preferred embodiment of the invention is restriction enzymes or derivatives thereof which do not contain N-formyl methionine. Particularly preferred embodiments are those enzymes and derivatives which are substantially free of N-formyl methionine, which therefore does not engender an adverse immunological reaction in a patient, or substantially reduces such adverse reactions in comparison with the enzymes and derivatives prior to removal of the N-formyl group.

It will be understood that in this context substantially free means that nearly all of the protein in a preparation lacks the N-formyl group, or that at least enough of the protein lacks the group to preclude or greatly ameliorate any adverse reaction to the group that its presence otherwise would engender.

The N-formyl group can be removed by chemical treatment. Alternatively, enzymes without N-formyl groups can be produced by recombinant DNA techniques. For instance, an enzyme of the invention may be produced via a cloned gene in *E. coli* as a fusion protein. Following purification, the fusion protein is proteolytically or chemically cleaved to produce the enzyme of interest and an N-terminal peptide containing the N-formyl methionine. The two products are then separated using well known techniques. Thus, enzymes of the invention can be produced without N-formyl groups to avoid the deleterious immunological effect such groups engender.

Another way to avoid unwanted immunological reactions is to conjugate a restriction endonuclease or derivative thereof to polyethylene glycol ("PEG") or polypropylene glycol ("PPG") (preferably of 500 to 20,000 daltons average molecular weight (MW)). Conjugation with PEG or PPG, as described by Davis et al., U.S. Pat. No. 4,179,337, for instance, can provide non-immunogenic, physiologically active, water soluble restriction enzyme conjugates with anti-viral activity. Similar methods also using a polyethylene—polypropylene glycol copolymer are described in Saifer et al., U.S. Pat. No. 5,006,333.

Additional methods that prevent or mitigate unwanted immunological response to the restriction endonucleases and derivatives thereof may also be used in accordance with the invention to provide safe and effective prophylactic, therapeutic and disinfectant agents.

The enzymes and enzyme derivatives of the invention also may be modified in other ways. Upon entry into a eukaryotic cell a restriction enzyme may be glycosylated, for instance. In some instances the glycosylation may be undesirable. Often glycosylation occurs only at certain amino acid sequences called glycosylation signals. Recombinant DNA techniques can be used to make enzymes of the invention that are not glycosylated at these sequences. Thus, DNA encoding an enzyme can be modified to alter the signal sequence so that it is not glycosylated. This will be useful where eukaryotic glycosylation occurs when the enzyme is administered to a patient and the glycosylation inhibits its activity, directly or by facilitating circulatory clearance, for instance.

The enzymes of the invention can be affected by other post-translational modifications and similar manipulations of amino acid sequence can be used to alter these modifications. Modification sites also can be introduced into an enzyme of the invention to engender a desirable modification as well.

Restriction enzymes of the invention may comprise targeting moieties, such as receptor binding domains, or an antibody binding region specific for a virus or host cell to which the enzyme is to be directed.

For instance, an enzyme of the invention may be conjugated to an antibody to provide targeting to a site of interest. As an example an antibody combining region specific for an exposed virion determinant may be conjugated to a restriction enzyme or derivative thereof for targeting the enzyme to the virus. The enzyme might then penetrate the virion and cleave viral genomic DNA that is double-stranded. Alternatively, binding of the conjugate to the virus might facilitate entry of the conjugate into cells, along with the virus particle. Co-infection of this type may increase the effectiveness of the endonucleolytic activity of the conjugate in inactivating virus.

Enzymes and enzyme derivatives of the invention also can be modified to alter structural features that affect their ability to enter a cell nucleus. For instance, enzymes and derivatives within a particular range of molecular weights may be preferred for this purpose in the invention. For instance, if a low molecular weight restriction enzyme is toxic in in vivo studies, which may be the case if it diffuses into the nucleus and deleteriously affects genomic DNA, natural or engineered enzymes in the range of 60,000 daltons or above may be used. Proteins of this molecular weight generally will not diffuse into the nucleus. Furthermore, to prevent active transport of enzymes into the nucleus, any nuclear targeting sequences present in the amino acid sequence of an enzyme or enzyme derivative may be removed by site specific mutagenesis techniques as described above.

Commercially available restriction enzymes are formulated to act on purified DNA under well-defined conditions, which are markedly different from physiological conditions, the conditions in stored blood and blood products, and the conditions presented by disinfectant applications. Accordingly, the enzymes of the invention may be modified, as described hereinabove, to provide optimal activity under these conditions.

Furthermore, enzymes of the invention will be formulated in accordance with their anti-viral application. Thus, for therapeutic use the enzymes preferably are substantially pure, and, in addition, pyrogen-free. As is well known, a variety of potent pyrogens are ordinary contaminants of biological preparations, such as commercially available restriction enzymes. Preparations that are not contaminated by pyrogens are preferred in the invention for any application wherein the enzymes will be administered to a patient. Furthermore, as discussed elsewhere herein, the enzymes preferably also are modified to reduce or prevent deleterious immunological reactions.

The pharmaceutical industry has long been able to prepare pyrogen-free preparations of hormones and other therapeutically useful proteins. For instance, see REMINGTON'S PHARMACEUTICAL SCIENCES (18th ed. 1990) (Mach Publishing Co., Easton Pa.), at page 1550. During the past decade the variety of medically useful proteins has increased markedly, in part due to the development of methods to clone genes and express the genes in heterologous organisms. The most notable of the heterologous organisms presently employed for recombinant expression of pharmaceutical proteins is *E. coli*, which has served as a host for the production of such recombinantly produced human protein and derivatives as growth hormone, insulin, tissue plasminogen activator, and a variety of interleukins, among others.

By applying well-known techniques of protein purification for each of these proteins it has been possible to prepare substantially pure and pyrogen-free preparations suitable for administration to human patients. The same techniques can be used to prepare substantially pure and pyrogen-free preparations of enzymes of the invention that are suitable for use in human patients. See Prior (1991) *BioTechnology* 17: 445–78 for a recent discussion of large-scale purification of clinical products from animal cell cultures.

It is notable in this regard that the genes of many restriction enzymes have been cloned and the enzymes expressed in active form in *E. coli*. "NEW ENGLAND BIOLABS, INC" 1991–1992 catalog, for instance, notes several restriction enzymes made by expression of cloned genes in *E. coli*. Thus, techniques similar to those developed for preparing from *E. coli* pyrogen-free insulin, growth hormone, tissue plasminogen activator, and interleukins will be particularly useful for preparing pyrogen-free restriction enzymes and derivatives, in accordance with the invention, from *E. coli*.

It will be appreciated that other organisms suitable to the expression of cloned genes and the preparation of the expressed proteins as substantially pure and pyrogen-free products also can be used in the invention.

It will be understood that a pyrogen-free preparation of an enzyme or enzyme derivative of the invention is a preparation that is free of pyrogens or contains only very small amounts of them and, therefore, does not produce a fever in a patient that interferes with use of the enzyme or derivative as a therapeutic agent.

Typically, for therapeutic applications, one or more enzymes or derivatives thereof will be combined with a pharmaceutically acceptable excipient appropriate to a planned route of administration. A variety of pharmaceutically acceptable excipients are well known, from which those that are effective for delivering restriction enzymes to a site of infection may be selected. The HANDBOOK OF PHARMACEUTICAL EXCIPIENTS published by the American Pharmaceutical Association is one useful guide to appropriate excipients for use in the invention. A composition is said to be a "pharmaceutically acceptable excipient" if its administration can be tolerated by the recipient. Sterile phosphate-buffered saline is one example of a pharmaceutically acceptable excipient that is appropriate for intravenous administration.

For purposes of therapy, one or more enzymes, or derivatives thereof, and a pharmaceutically acceptable excipient are administered in a therapeutically effective amount. Such a combination is said to be administered in a "therapeutically effective amount" if the amount administered is physiologically significant. An agent is physiologically significant if its presence results in a detectable change in the physiology of the recipient. In the present context, an agent is physiologically significant if its presence results in a decrease in the severity of one or more symptoms of a viral illness.

Administration may be topical or internal, or by any other suitable avenue for introducing a therapeutic agent to a patient. Topical administration may be by application to the skin, or to the eyes, ears, or nose. Internal administration may proceed intradermally, subcutaneously, intramuscularly, intraperitoneally, intraarterially or intravenously, or by any other suitable route. It also may in some cases be advantageous to administer a composition of the invention by oral ingestion, by respiration, rectally, or vaginally. For a brief review of pharmaceutical dosage forms and their use, see PHARMACEUTICAL DOSAGE FORMS AND THEIR USE (1985) (Hans Huber Publishers, Berne, Switzerland).

The formulations used to administer the enzymes of invention are tailored to the planned route of administration to provide appropriate localization and rates of exposure to the enzyme composition. For instance, the enzymes of the invention may be administered in readily soluble form, so as to enter the circulation quickly. Alternatively, the persistence of the enzymes in circulation may be enhanced by conjugating the enzymes with polyethylene glycol or polypropylene glycol or mixtures thereof, as described hereinabove.

Liposome encapsulation of restriction endonucleases provides an alternative method for administering the enzymes. Liposomes are microscopic vesicles that consist of one or more lipid bilayers surrounding aqueous compartments. See, generally, Bakker-Woudenberg et al., *Eur. J. Clin. Microbiol. Infect. Dis.* 12 (Suppl. 1): S61 (1993), and Kim, *Drugs* 46: 618 (1993). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s). See, for example, Machy et al., LIPOSOMES IN CELL BIOLOGY AND PHARMACOLOGY (John Libbey 1987), and Ostro et al., *American J. Hosp. Pharm.* 46:1576 (1989). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents. Scherphof et al., *Ann. N.Y. Acad. Sci.* 446:368 (1985).

After intravenous administration, conventional liposomes are preferentially phagocytosed into the reticuloendothelial system. However, the reticuloendothelial system can be circumvented by several methods including saturation with large doses of liposome particles, or selective macrophage inactivation by pharmacological means. Claassen et al., *Biochim. Biophys. Acta* 802: 428 (1984). In addition, incorporation of glycolipid- or polyethelene glycol-derivatised phospholipids into liposome membranes has been shown to result in a significantly reduced uptake by the reticuloendothelial system. Allen et al., *Biochim. Biophys. Acta* 1068: 133 (1991); Allen et al., *Biochim. Biophys. Acta* 1150: 9 (1993) These Stealth® liposomes have an increased circulation time and an improved targeting to tumors in animals. Woodle et al., *Proc. Amer. Assoc. Cancer Res.* 33:2672 (1992). Human clinical trials are in progress, including Phase III clinical trials against Kaposi's sarcoma. Gregoriadis et al., *Drugs* 45:15 (1993).

In vitro studies indicate that intracellular viral infections in nonphagocytic cells can be more effectively treated when the antiviral agent is administered in a liposome-encapsulated form. Szoka et al., *Antimicrobial Agents and Chemotherapy* 32: 858 (1988), and Bakker-Woudenberg et al., *Scand. J. Infect. Dis.* 23 (Suppl. 74): 54 (1991). For example, the antiviral agents ganciclovir and foscarnet inhibited viral replication in cytomegalovirus-infected human lung fibroblast cells at levels that were 6-fold and 115-fold greater, respectively, when the agents were liposome encapsulated. Bakker-Woudenberg et al., supra. Thus, liposome encapsulation provides a particularly suitable method for administering restriction endonucleases to inhibit viral propagation.

Restriction endonucleases can be encapsulated within liposomes using standard techniques of protein microencapsulation. See, for example, Anderson et al., *Infect. Immun.* 31:1099 (1981), Anderson et al., *Cancer Res.* 50:1853 (1990), and Cohen et al., *Biochim. Biophys. Acta* 1063: 95 (1991). A preferred method of encapsulating restriction enzymes is described in Example 3. This method is based upon the technique of Alving et al. "Preparation and Use of Liposomes in Immunological Studies," in LIPOSOME TECHNOLOGY (2nd Edition), Vol. III, (Gregoriadis, ed.), page 317 (CRC Press 1993), which is incorporated by reference. Also, see Wassef et al., *Meth. Enzymol.* 149:124 (1987).

As noted above, therapeutically useful liposomes may contain a variety of components. For example, liposomes may comprise lipid derivatives of poly(ethylene glycol). Allen et al. (1993), supra. A preferred form of liposome useful for restriction enzyme encapsulation comprises phospholipids and cholesterol in a 2:1.5 molar ratio, which approximates the ratio of lipids found in erythrocytes. Preferably, the phospholipid is dimyristoylphosphatidylcholine, although, liposomes may further comprise one or more additional phospholipids selected from the group consisting of dimyristoylphosphatidylglycerol, phosphatidylserine, phosphatidylinositol, phosphatidylinositol phosphate and dipalmitoylphosphatidic acid. More preferred forms of liposome comprise dimyristoylphosphatidylcholine and dimyristoylphosphatidylglycerol, as described by Alving et al., supra.

Liposomes can be prepared for targeting to particular cells or organs by varying phospholipid composition or by inserting receptors or ligands into the liposomes. For instance, antibodies specific to the determinants of the envelope of the hepatitis B virus may be incorporated into liposomes, together with an enzyme of the invention, to target the liposome more effectively to cells expressing the viral protein. Or the enzyme itself may comprise a targeting antibody combining region. Similar methods can be used to direct enzymes to the virions or envelopes of other viruses in the same way.

Liposomes may be administered to a subject intravenously, intraperitoneally, intrathecally, intramuscularly or subcutaneously. See, for example, Kim, supra, Bakker-Woudenberg et al. (1993), supra, Allen et al. (1993), supra, and Fielding et al., *Clin. Pharmacokinetics* 21:155 (1991). Preferably, liposome-encapsulated restriction enzyme preparations are administered intravenously.

In general, the dosage of administered liposome-encapsulated restriction enzymes will vary depending upon such factors as the patient's age, weight, height, sex, general medical condition and previous medical history. Dose ranges for particular formulations can be determined by using a suitable animal model. For example, mice having the murine acquired immunodeficiency syndrome provide a suitable model for determining efficacious dosages of EcoRI for the treatment of a disease caused by a virus that is susceptible to EcoRI cleavage.

The present invention also contemplates compositions comprising restriction enzymes that are formulated for prophylactic treatment of biologically derived products and products intended for biological use that are subject to viral contamination. Among such products are blood and blood products. HIV and hepatitis B virus, for instance, are fatal or potentially fatal contaminants of blood and some blood derivative products, which can be treated by methods of the present invention.

For inactivating virus in blood a composition comprising a substantially non-immunogenic, pyrogen-free enzyme of the invention, which is effective to inactivate virus in the blood or blood product, is added to the blood or blood derivative, and incubated under conditions suitable to the blood or blood product and the activity profile of the enzyme to substantially inactivate the virus.

It will be advantageous in some cases to incorporate enzymes of the invention in a liposome prior to addition to the blood or blood product, to increase the persistence and activity of the enzyme, for instance. Of course, other means can be used in accordance with the invention to increase the persistence, activity and effectiveness of restriction enzymes for inactivating virus in blood and blood products, inter alia.

Similarly, it is desirable to improve the efficacy of enzymatic inhibition by facilitating entry into infected cells. For instance, enzymes of the invention may be associated with virus to enter the cell. One way to improve entry, therefore, is to augment the ability of the enzyme to associate with the virus envelope or virion or the like. Association also keeps the enzyme in the vicinity of the virus, and, therefore, in proximity to the double-stranded DNA form of the genome.

For topical and internal therapeutic applications enzymes of the invention can be formulated using any suitable pharmacological technique. For instance, the enzymes can be formulated for prolonged release. As described hereinabove, persistence of anti-viral enzymatic activity may be increased or modulated by incorporating restrictions enzymes or derivatives thereof into liposomes.

Other methods are also useful in the invention in this regard. For instance, one method suitable for use in the invention was described by Cardinal et al., U.S. Pat. No. 4,895,724. An enzyme of the present invention is dispersed in a porous chitosan that has been treated as described by Cardinal et al. to provide timed release of the enzyme at the site of implantation of the porous chitosan.

It will be appreciated, in any case, that the plethora of pharmaceutical methods for formulating and administering agents can be used in accordance with the invention to deliver an effective dose to a site of infection for an appropriate period of time to have a preventive, ameliorative or curative effect.

The present invention, thus generally described, will be understood more readily by reference to the following examples, which are provided by way of illustration and are not intended to be limiting of the present invention.

EXAMPLE 1

HIV Infection of Cultured PBL's is Inhibited by Restriction Enzymes in the Media The ability of restriction enzymes specific for sequences known to be in the double-stranded DNA form of HIV could suppress HIV infection of human peripheral blood lymphocytes in vitro. Two enzymes that cleave purified double-stranded HIV DNA, and have optimal activity under lymphocyte culture conditions of approximately neutral pH and 37° C., were tested for their ability to inhibit infection in this assay. Another enzyme having a similar activity profile, which does not cleave double-stranded HIV DNA was used as a negative control.

Figure 1A:
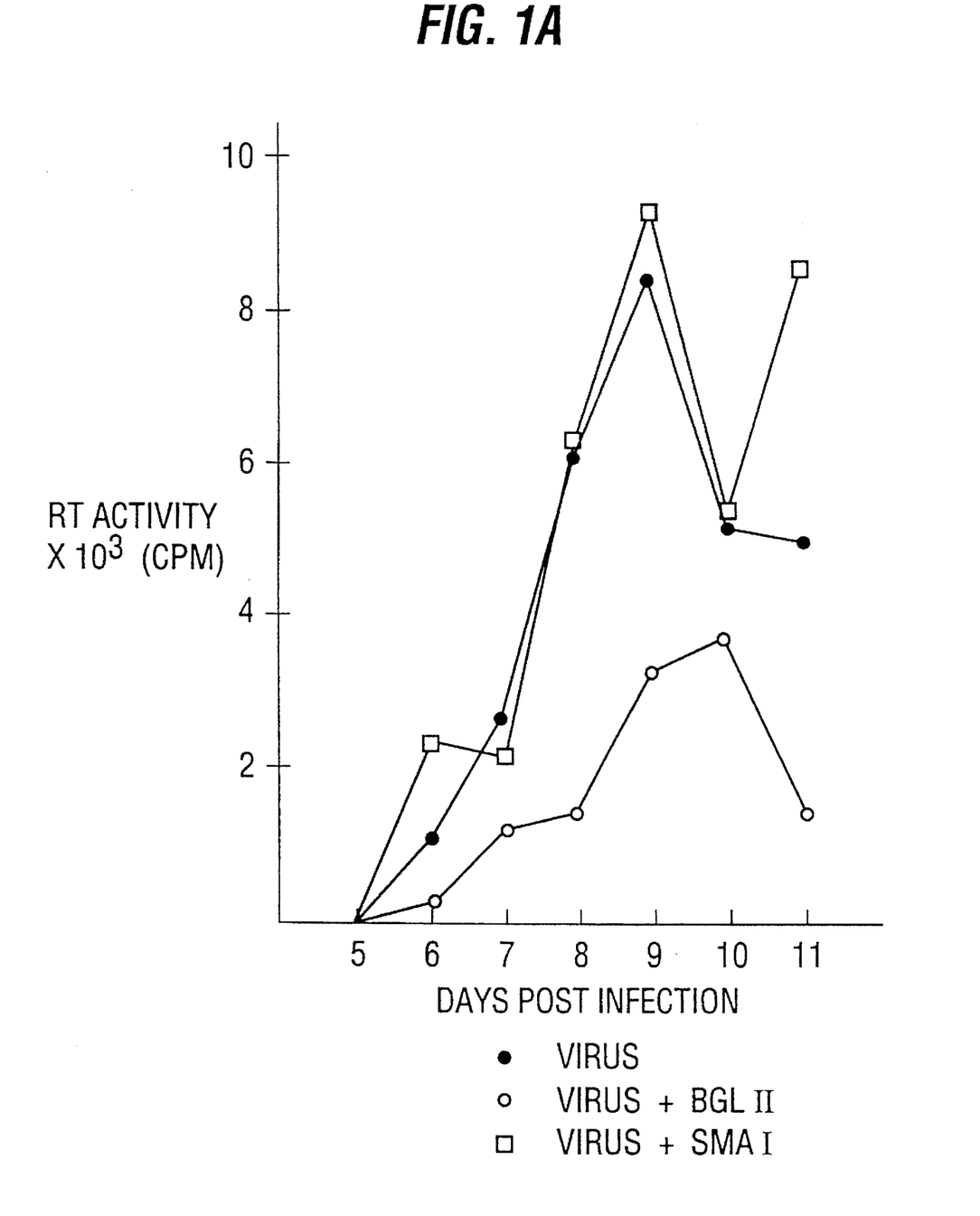
FIG. 1A is a graph showing the development of reverse transcriptase activity in culture supernatants after exposure of human peripheral blood lymphocytes to HIV, when the cells were cultured in the presence of restriction enzymes added during the adsorption phase and daily throughout the culture. The results show inhibition of viral infection by BglII.
Figure 1B:
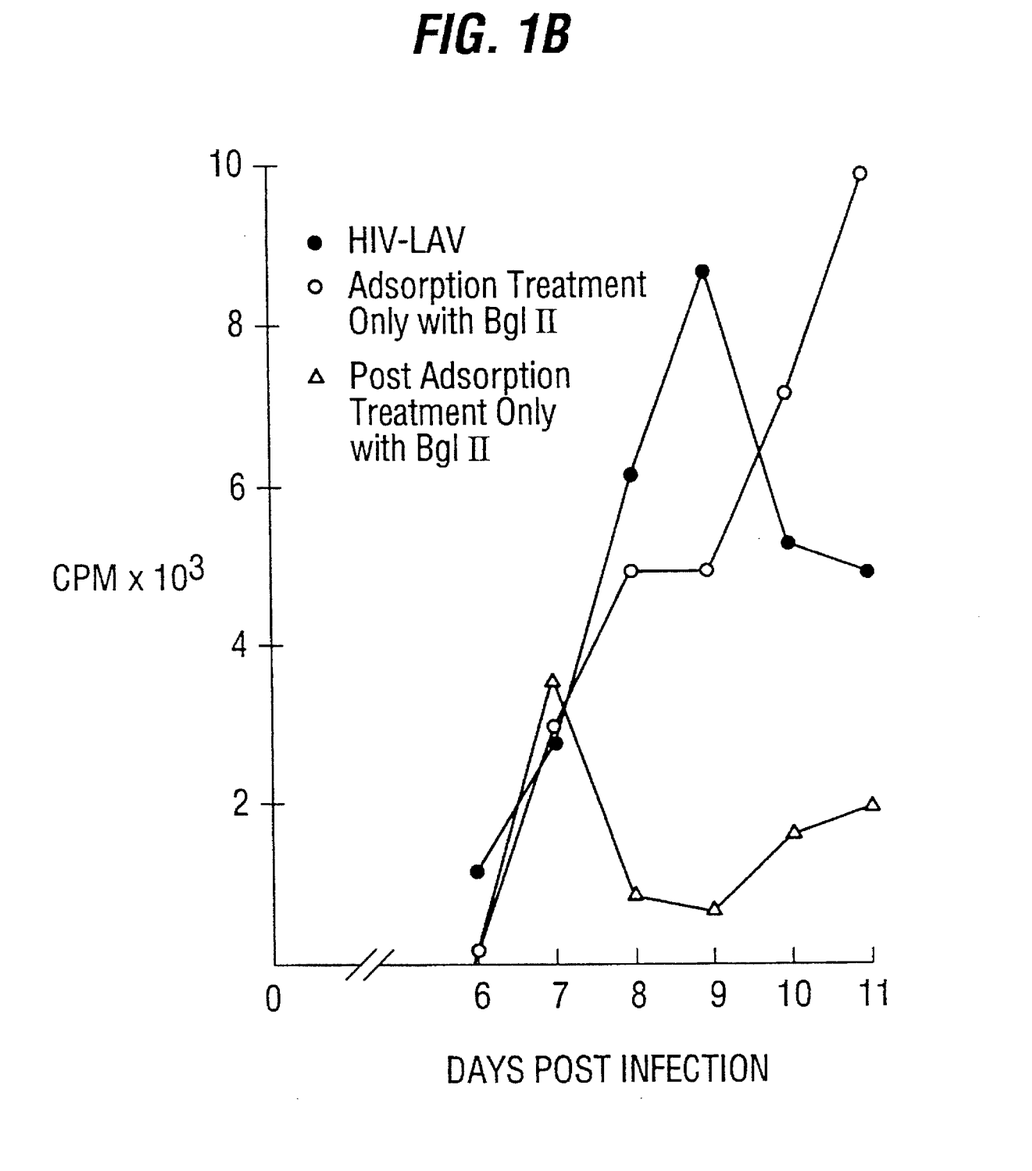
FIG. 1B is a graph showing the development of reverse transcriptase activity in culture supernatants after exposure of human peripheral blood lymphocytes to HIV, when the cells were exposed to BglII only during the adsorption phase or during post-infection culturing. The results show that viral infection was inhibited when cells were cultured after infection in the presence of the enzyme.

As shown in FIG. 1, the enzyme BglII, which is known to cleave the viral dsDNA at multiple sites including the LTR region of the virus, retards the development of reverse transcriptase (RT) activity in culture supernatants, a measure of viral infection. This is so when the enzyme is added during the adsorption phase and throughout the period of culturing (FIG. 1A) or after the adsorption phase of the infection and throughout the period of culturing (FIG. 1B). When the enzyme is added both during the adsorption of the virus and daily throughout the time the cells are cultured, the rise in RT activity is delayed with respect to the control infection and the peak of RT activity is less than half of the control infection.

The enzyme KpnI, that cleaves fewer sites, and does not cleave throughout the length of the viral dsDNA, also inhibited the development of RT activity in culture supernatants. The results obtained with KpnI depended on the commercial preparation of the enzyme that was used to a greater extent than was the case for BglII. The variability could be attributed to differences between the KpnI preparations, rather than to variations in the ability of enzyme itself to cleave the DNA.

Visual observation of the course of the infection correlated with the development of RT activity. The appearance of multinucleate giant cells and syncytia presaged the rise of RT activity in the cultures. The appearance of these markers also was delayed in cultures treated with BglII.

The enzyme, SmaI, which does not cut the double-stranded HIV DNA at all, also does not interfere with the course of viral infection as measured by RT activity.

Figure 2:
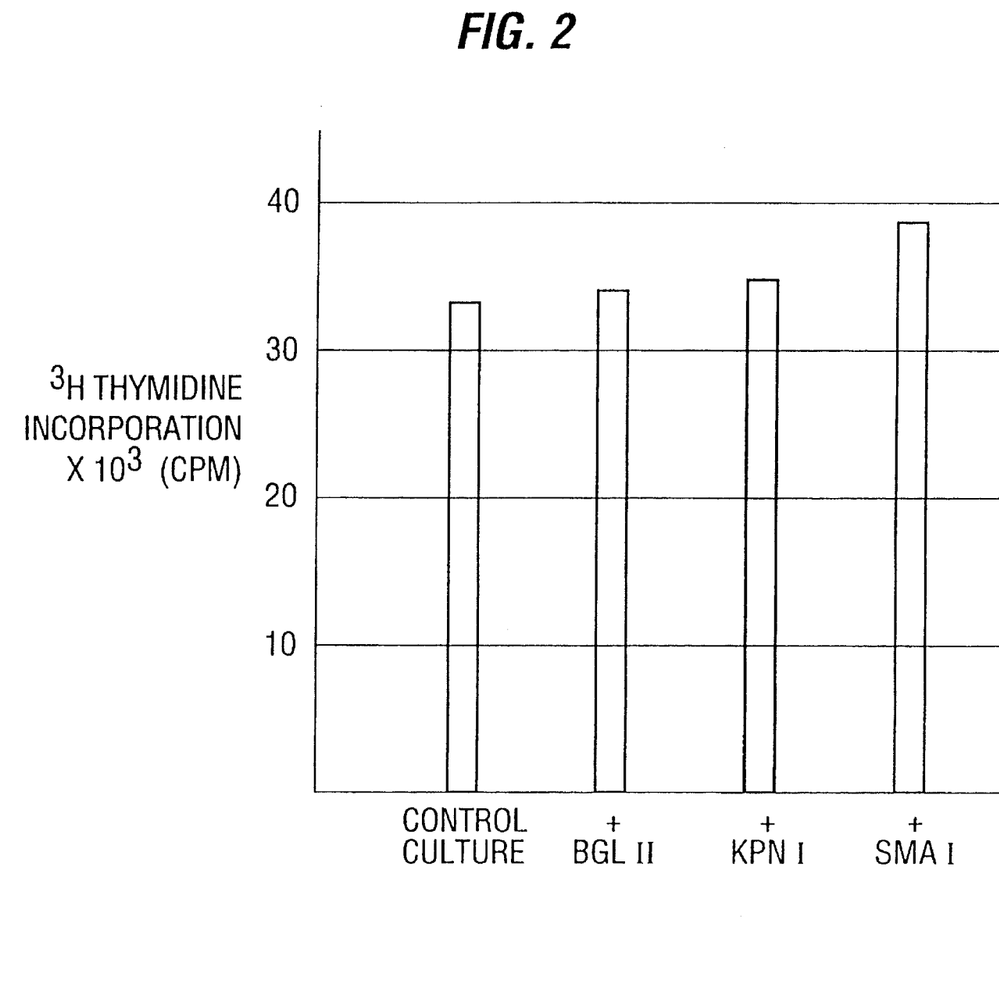
FIG. 2 is a bar graph showing $^3$H-thymidine incorporation in cells cultured under standard conditions and under the same conditions in the presence of BglII, KpnI, or SmaI. The results show that the restriction enzymes did not affect cell growth after 24 hours in culture.

As shown in FIG. 2 none of the enzymes caused an adverse effect on cell proliferation in a short term assay in the absence of virus. Thus, the inhibition of viral infection observed using BglII cannot be attributed to a deleterious effect of the enzyme on cell-proliferation, and the results show that an enzyme that cuts often in the double-stranded viral DNA inhibits HIV infection.

EXAMPLE 2

Inactivation of Hepatitis B Virus in Blood and Blood Products

Hepatitis B remains one of the most common serious viral infections of mankind. Some of those who are infected become carriers of the virus, and those carriers constitute the viral reservoir for new infections. These carriers often have high titers of the virus in their circulation.

Blood obtained from a patient infected with hepatitis B that contains hepatitis B virus is treated with a mixture of restriction enzymes known to cut the virus at several sites, including the enzymes EcoRI, BamHI, and XbaI. The blood is assayed for cleavage of hepatitis B DNA. No intact viral DNA is detected.

In a parallel, control experiment, an aliquot of the same blood sample is treated with the same enzyme mixture first inactivated by heat treatment. The mock-treated blood is then assayed for intact viral DNA. The viral DNA remains intact in the control experiment.

EXAMPLE 3

Liposome Encapsulation of Restriction Endonucleases

To examine the stability of liposome-encapsulated restriction endonucleases, liposomes were produced that contained either KpnI or EcoRI. Liposomes were prepared as described by Alving et al., supra. Briefly, liposomes were made from stock solutions of lipids of known molarity in chloroform or chloroform-methanol (2:1, v/v). Dimyristoylphosphatidylcholine, dimyristoylphosphatidylglycerol and cholesterol were mixed in a flask at a molar ratio of 0.9:0.1:0.75. The mixture was dried in a rotary evaporator under mild negative pressure and then, the mixture was dried overnight under a very high vacuum (<50 μm Hg) in a desiccator.

Multilamellar vesicles were formed by dispersing and suspending the dried lipids in sterile pyrogen-free water. The final phospholipid concentration in the aqueous dispersion was about 30 to 40 mM. The aqueous liposomes were then transferred to lyophilizer bottles and the mixture was lyophilized. Lyophilized liposomes were reconstituted at 100 mM to 200 mM phospholipid in liposome buffer (Dulbecco's phosphate-buffered saline without calcium chloride or magnesium chloride [Life Technologies, Inc.; Gaithersburg, Md.]) alone, or in liposome buffer containing restriction endonuclease.

Preparations containing enzymes were washed to remove unencapsulated enzyme by diluting the liposome preparation by about 20-fold in buffer and then, centrifuging the diluted mixture at 29,000 ×g. After centrifugation, supernatants were aspirated and liposomal pellets were resuspended in buffer at a concentration of about 140 mM phospholipid. Liposome-encapsulated enzyme preparations contained KpnI (United States Biochemical Corp.; Cleveland, Ohio) at a concentration of 1200 units per milliliter of liposome preparation, or EcoRI (Life Technologies, Inc.) at a concentration of 10,000 units per milliliter of liposome preparation.

Routine lambda DNA digestion assays confirmed that liposome encapsulation did not inactivate the activity of either restriction endonuclease. Moreover, the liposome-encapsulated enzymes were found to retain their specific restriction endonuclease activities after two months of storage at 4° C.

Thus, formulations of liposome-encapsulated restriction enzymes retain enzymatic activity over several months of storage at 4° C.

EXAMPLE 4

Studies on the Toxicity of Liposome-Encapsulated Restriction Endonucleases

Toxicology of restriction endonuclease liposomes was examined in six C57BL/6 mice. Three animals received 0.2 milliliters of the KpnI-liposome preparation or the EcoRI-liposome preparation intraperitoneally every third day for three weeks. After three weeks, two of the three animals from each group were sacrificed and sent to a veterinary pathologist for evaluation.

The results of these studies demonstrated that treatment with the liposome-encapsulated restriction enzymes did not induce specific toxic side effects. Moreover, the remaining animal from each group remained alive for four months after the initiation of the study.

Thus, the intraperitoneal administration of liposome-encapsulated restriction endonucleases is well-tolerated by mice.

EXAMPLE 5

The Use of Liposome-Encapsulated Restriction Endonucleases as Antiviral Agents In Vivo The effectiveness of restriction endonucleases as antiviral agents was examined using the MAIDS model, described above. In this experiment, mice were injected with LP-BM5 retroviruses to induce MAIDS and then treated with a liposome-encapsulated EcoRI preparation. EcoRI was chosen for this study because the enzyme cleaves a helper virus that is considered to be essential for the development of MAIDS. The LP-BM5 retroviral mix was obtained from Dr. Janet W. Hartley and Dr. Herbert C. Morse III (National Institute of Allergy and Infectious Diseases; Bethesda, Md). Descriptions of the LP-BM5 mixture may be found, for example, in Hamelin-Bourassa et al., Immunogenetics 30: 266 (1989), Hartley et al., *J. Virol.* 63: 1223 (1989), and Chattopadhyay et al., *J. Virol.* 65: 4232 (1991), which are incorporated by reference.

In these studies, there were six groups of C57BL/6N mice with ten animals in each group: (1) a control group of uninfected mice; (2) a control group of uninfected mice that received liposomes containing buffer alone; (3) a control group of uninfected mice that received the EcoRI-liposome preparation; (4) a group of infected mice that received no treatment following infection; (5) a group of infected mice that were treated with liposomes containing buffer alone; and (6) a group of infected mice that were treated with the EcoRI-liposome preparation. MAIDS was induced by injecting mice with 100 μl of the LP-BM5 virus mixture. The EcoRI-liposome preparation contained 12,500 units of EcoRI and 140 μmoles of phospholipid per milliliter of liposome preparation. Liposome treatments began 24 hours after infection and were repeated every three days for eight weeks. Mice received 200 μl of liposome preparation per injection.

Figure 3:
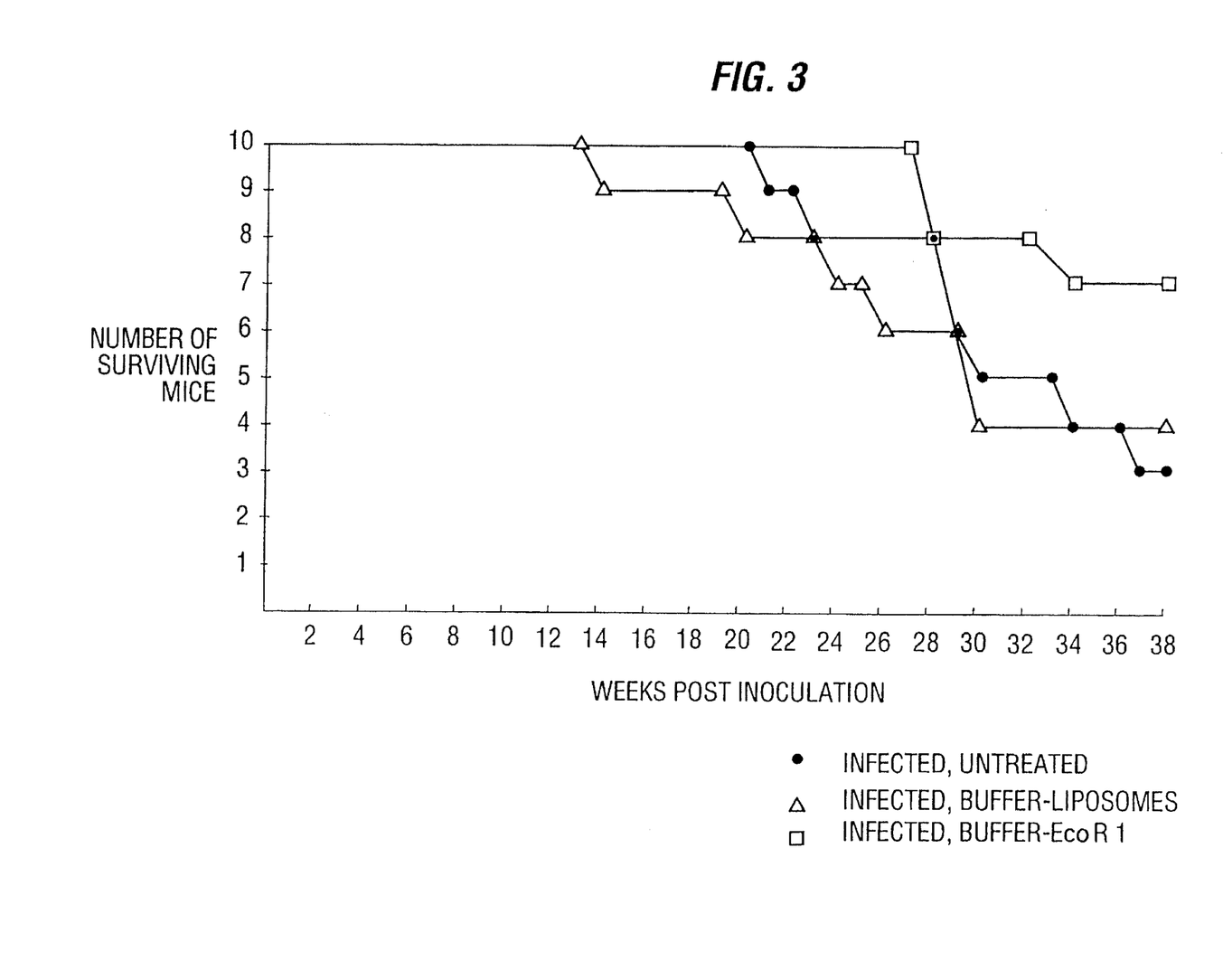
FIG. 3 is a graph showing the survival rate of mice that had been infected with the LP-BM5 mixture of murine leukemia viruses. The infected mice were either untreated, treated with liposomes containing buffer, or treated with liposomes containing EcoRI. The results show that treatment with the EcoRI-liposome preparation increased the survival rate of infected mice.
Figure 4:
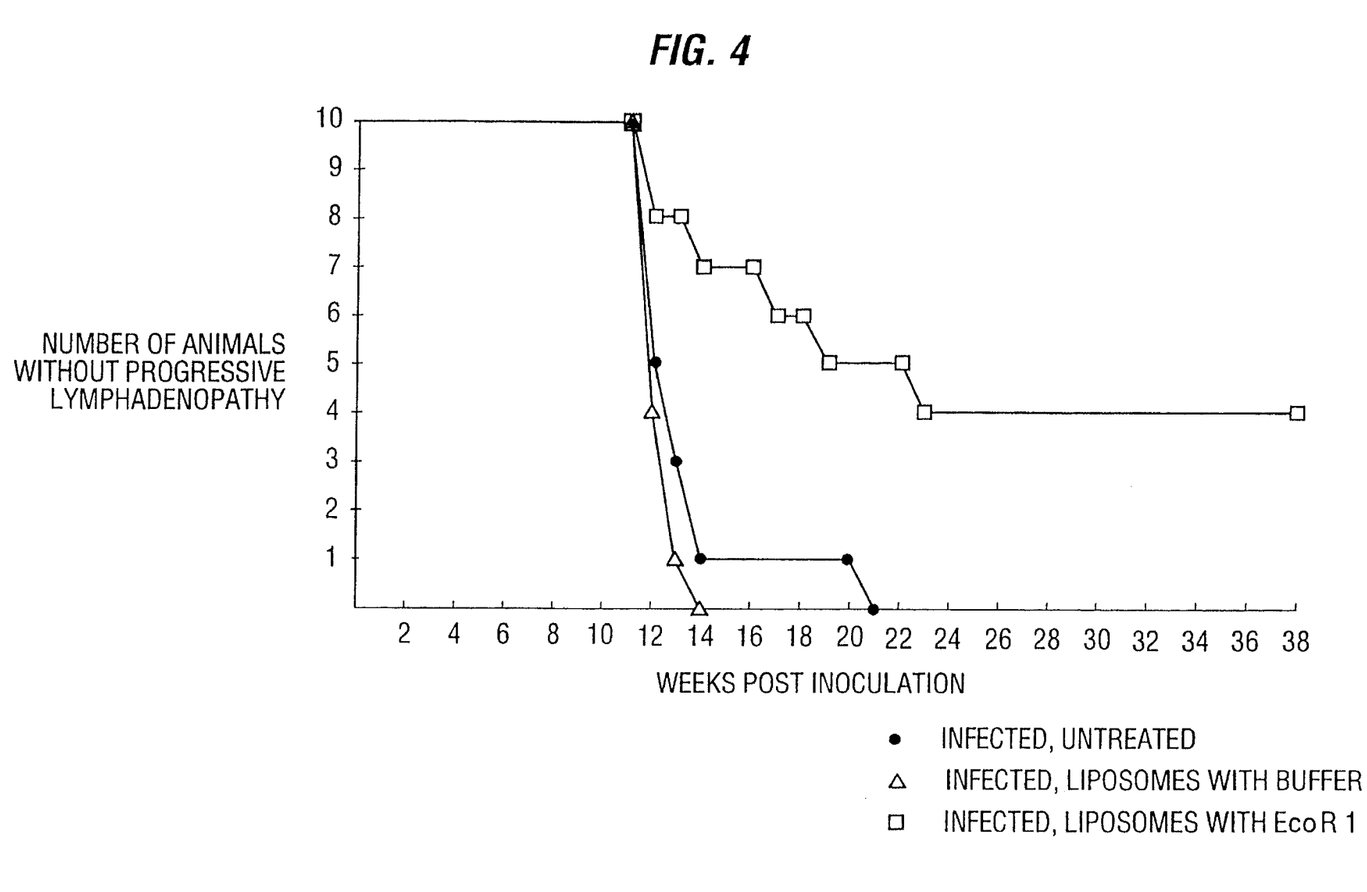
FIG. 4 is a graph showing the onset of progressive lymphadenopathy in mice that had been infected with the LP-BM5 mixture of murine leukemia viruses. The infected mice were either untreated, treated with liposomes containing buffer, or treated with liposomes containing EcoRI. The results show that treatment with the EcoRI-liposome preparation decreased the rate of disease onset in infected mice.

As shown in FIG. 3, treatment with the EcoRI-liposome preparation increased the survival rate of infected mice. Moreover, FIG. 4 shows that treatment with the EcoRI-liposome preparation decreased the rate of disease onset in infected mice, as determined by the development of progressive lymphadenopathy.

To examine possible toxic side effects of treatment, the groups of uninfected control mice were treated with the control and experimental liposome preparations. These control animals received injections every third day for eight weeks. After eight months, mice treated with buffer-containing liposomes or the restriction enzyme-liposome preparation showed no obvious signs of toxicity, and none of the animals has expired.

EXAMPLE 6

Amelioration of Warts by Topical Application of Restriction Enzyme Compositions Papovaviruses provide other examples of agents of human disease that can be treated with restriction enzymes in accordance with the invention. Warts caused by papovaviruses are treated by topical application of compositions that provide restriction enzyme activity.

A patient with *Verrucae vulgaris* on both hands is treated on one hand with an ointment containing a combination of restriction enzymes that cleave the viral DNA. The other hand is treated in the same way but the enzymes in the ointment are inactivated. The lesions on the treated hand clear. The ones on the untreated hand persist.

EXAMPLE 7

Amelioration of Cold Sores Caused by Herpes Simplex 1 Using Topical Application of Restriction Enzymes Several patients with cold sores on both sides of their mouths, are treated on one side only with an ointment containing a combination of restriction enzymes that cleave the HSV-1 viral DNA. The other side is treated in the same way, but the ointment contains only inactive enzymes. The lesions on the treated side clear more quickly than those on the untreated side. The difference in clearing rates is statistically significant and shows the efficacy of the enzymes in the topical preparation.

Two groups of patients with cold sores are treated. One group is treated with an ointment containing a combination of restriction enzymes that cleave the HSV-1 viral DNA. The other group is treated is the same way, but the ointment contains only inactive enzymes. In the group treated with the active preparation the sores heal more quickly than in the group treated only with inactivated enzymes. The difference between the healing rates of the two groups is statistically significant and shows a positive therapeutic effect of topical application of the enzyme preparation on healing cold sores.

EXAMPLE 8

Treatment of AIDS with Restriction Enzymes

HIV positive patients are treated daily with a parenteral or oral formulation containing a combination of restriction enzymes that cleave HIV DNA under physiological conditions. The incidence of opportunistic infections in this group is significantly lower than in a statistically matched control group, showing that the parenteral formulation is arresting the progress of the disease.

Analysis of T cells that are CD4 positive also shows the therapeutic effect of the restriction enzymes. CD4 positive T cell levels are steady or increase in patients treated with restriction enzymes, whereas patients in the untreated matched control show a decline in CD4 positive T cells over the same period of time.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patents mentioned in this specification are indicative of the level of skill of those in the art to which the invention pertains. All publications and patents are herein incorporated by reference to the same extent as if each individual publication or patent was specifically and individually indicated to be incorporated by reference in its entirety.

What is claimed is:

1. A method for inhibiting propagation of a virus, comprising the step of administering to a patient in a therapeutically effective amount a composition comprising a compound comprised of a moiety of a restriction endonuclease such that said moiety displays endonucleolytic activity toward the DNA of said virus.

2. The method of claim 1, wherein said composition comprises a pharmaceutically acceptable excipient.

3. A method for inhibiting propagation of a virus, comprising the step of administering to a patient in a therapeutically effective amount a composition comprising a compound comprised of a moiety of a restriction endonuclease such that said moiety displays endonucleolytic activity toward the DNA of said virus, wherein said compound is encapsulated in a liposome.

4. The method of claim 3, wherein said compound is modified to decrease deleterious immunological side effects compared with the unmodified compound.

5. The method of claim 2, wherein said composition is administered internally.

6. The method of claim 5, wherein said composition is administered intradermally, subcutaneously, intramuscularly, intraperitoneally, intraarterially or intravenously.

7. The method of claim 6, wherein said compound is modified to decrease deleterious immunological side effects compared with unmodified compound.

8. The method of claim 7, wherein said compound is substantially free of N-formyl methionine.

9. The method of claim 7, wherein said compound is modified by conjugation to polyethylene glycol or polypropylene glycol.

10. The method of claim 2, wherein said virus is HIV.

11. The method of claim 10, wherein said restriction endonuclease moiety provides the endonucleolytic activity of the BglII restriction endonuclease.

12. The method of claim 2, wherein said virus is hepatitis B.

13. The method of claim 1, wherein said compound comprises an antigen specific binding region for localizing the endonucleolytic activity of said compound at a target site of infection where said antigen is located.

14. The method of claim 13, wherein said antigen is a HIV antigen.

15. An ex vivo method to inactivate virus in blood or a blood derived composition, comprising the step of exposing said blood or blood-derived composition to a compound comprised of a moiety of a restriction endonuclease that provides endonucleolytic activity of a type and in an amount effective to inactivate a virus.

16. A ex vivo method to inactivate virus in blood or a blood derived composition, comprising the step of exposing said blood or blood-derived composition to a compound comprised of a moiety of a restriction endonuclease that provides endonucleolytic activity of a type and in an amount effective to inactivate a virus, wherein said restriction endonuclease is encapsulated in a liposome.

17. The method of claim 15, wherein said compound is modified to decrease deleterious immunological side effects compared with the unmodified compound when said blood or blood-derived composition is administered to a patient.

18. The method of claim 15, wherein said compound is conjugated to polyethylene glycol or polypropylene glycol.

19. The method of claim 18, wherein said virus is selected from the group consisting of HIV, hepatitis B and hepatitis C.

20. The method of claim 19, wherein said virus is the HIV virus and said endonucleolytic activity is that of the BglII endonuclease.

21. A pharmaceutical composition for topical administration, comprising:

(A) a substantially pure and pyrogen-free compound comprised of a moiety of a restriction endonuclease such that said restriction endonuclease moiety displays endonucleolytic activity toward the DNA of a virus at a site of infection to which said composition is applied; and (B) a pharmaceutically acceptable excipient for topical administration.

22. The composition of claim 21, wherein said compound is substantially non-immunogenic for topical application.

23. The composition of claim 22, wherein said compound is substantially free of N-formyl methionine.

24. The composition of claim 22, wherein said compound is conjugated to polyethylene glycol or polypropylene glycol.

25. A pharmaceutical composition for systemic administration, comprising:

(A) a substantially pure and pyrogen free compound comprised of a moiety of a restriction endonuclease such that said restriction endonuclease moiety displays endonucleolytic activity toward the DNA of a virus at a site of infection; and, (B) a pharmaceutically acceptable excipient for systemic administration.

26. The composition of claim 25, wherein said compound is substantially non-immunogenic for systemic application.

27. The composition of claim 26, wherein said compound is substantially free of N-formyl methionine.

28. The composition of claim 26, wherein said compound is conjugated to polyethylene glycol or polypropylene glycol.

29. A disinfectant composition, comprising:

(A) a compound comprised of a moiety of a restriction endonuclease such that said restriction endonuclease moiety displays endonucleolytic activity toward the DNA of a virus when applied to an object to be disinfected; and (B) an inert carrier for disinfectant application.

30. A method for inhibiting propagation of a virus, comprising the step of topically administering to a patient in a therapeutically effective amount a composition comprising a compound comprised of a moiety of a restriction endonuclease such that said restriction endonuclease moiety displays endonucleolytic activity toward DNA of said virus.

31. The method of claim 30, wherein said composition further comprises a pharmaceutically acceptable excipient.

32. The method of claim 31, wherein said compound is modified to decrease deleterious immunological side effects compared with the unmodified compound.

33. The method of claim 30, wherein said compound is substantially free of N-formyl methionine.

34. The method of claim 30, wherein said compound is modified by conjugation to polyethylene glycol or polypropylene glycol.

35. The method of claim 31, wherein said virus is HIV.

36. The method of claim 35, wherein said moiety provides the endonucleolytic activity of the BglII restriction endonuclease.

37. The method of claim 31, wherein said virus is hepatitis B.

* * * * *